US012797094B2

(12) United States Patent
Fojtik

(10) Patent No.: US 12,797,094 B2
(45) Date of Patent: Nov. 17, 2026

(54) UNIBODY RETRIEVAL BASKETS AND METHODS

(71) Applicant: Control Medical Technology, LLC, Hallandale, FL (US)

(72) Inventor: Shawn P. Fojtik, Park City, UT (US)

(73) Assignee: Control Medical Technology, Inc., Hallandale, FL (US)

( * ) Notice: Subject to any disclaimer, the term of this patent is extended or adjusted under 35 U.S.C. 154(b) by 228 days.

(21) Appl. No.: 18/235,799

(22) Filed: Aug. 18, 2023

(65) Prior Publication Data

US 2024/0058025 A1 Feb. 22, 2024

Related U.S. Application Data

(60) Provisional application No. 63/399,196, filed on Aug. 18, 2022.

(51) Int. Cl.

| | |
|---|---|
| ***A61B 17/221*** | (2006.01) |
| ***A61B 17/22*** | (2006.01) |
| ***A61M 25/00*** | (2006.01) |
| *A61B 17/00* | (2006.01) |

(52) U.S. Cl.

CPC ...... *A61B 17/221* (2013.01); *A61B 17/22031* (2013.01); *A61M 25/0074* (2013.01); *A61B 2017/00867* (2013.01); *A61B 2017/2215* (2013.01)

(58) Field of Classification Search

CPC ................................................ A61B 17/22031
USPC .............................................................. 606/1
See application file for complete search history.

(56) References Cited

U.S. PATENT DOCUMENTS

| | | | | |
|---|---|---|---|---|
| 8,945,172 B2 | 2/2015 | Ferrera et al. | | |
| 10,939,932 B1 * | 3/2021 | Yang | A61B 17/221 | |
| 2008/0058834 A1 * | 3/2008 | Cheng | A61B 17/221 606/127 | |

(Continued)

FOREIGN PATENT DOCUMENTS

| | | |
|---|---|---|
| CN | 112617967 A | 4/2021 |
| JP | 2022500190 A | 1/2022 |

(Continued)

OTHER PUBLICATIONS

USPTO acting as International Searching Authority, "Search Report and Written Opinion," International Application No. PCT/US2023/030646, Dec. 21, 2023.

(Continued)

*Primary Examiner* — Nicole F Johnson
(74) *Attorney, Agent, or Firm* — DENTONS Durham Jones Pinegar

(57) ABSTRACT

A retrieval device, which removes objects from a body of a subject in conjunction with a catheter, includes a tube with an expandable section at or adjacent to its distal end. The expandable section may be a basket. The basket may self-expand or a user may manually control its expansion. Struts of the basket may rotate to facilitate engagement of (e.g., extension into, grasping of, etc.) the object that is to be removed from the subject's body. The retrieval device may also be used to selectively control aspiration through the catheter or the retrieval device. Methods of retrieving objects from the body of a subject are also disclosed, as are methods for forming expandable sections of medical devices, such as retrieval devices.

22 Claims, 6 Drawing Sheets

(56) References Cited

U.S. PATENT DOCUMENTS

| | | | |
|---|---|---|---|
| 2017/0112515 | A1 | 4/2017 | Eamon et al. |
| 2020/0085456 | A1 | 3/2020 | Shamay et al. |
| 2020/0093618 | A1 | 3/2020 | Fojtik |
| 2021/0315599 | A1 | 10/2021 | Vale et al. |

FOREIGN PATENT DOCUMENTS

| | | | | |
|---|---|---|---|---|
| WO | WO-2008027953 | A2 * | 3/2008 | ........... A61B 17/221 |
| WO | 2020-061589 | A1 | 3/2020 | |

OTHER PUBLICATIONS

Japan Patent Office, "Reasons for Rejection," Japanese Patent Application No. 2025-510359, Jan. 9, 2026.

European Patent Office, Communication pursuant to Rule 62 EPC—supplementary European Search Report, European Patent Application No. 26855529.6, Jun. 22, 2026.

European Patent Office, Communication pursuant to Rules 70(2) and 70a(2) EPC, European Patent Application No. 23855529.6, Jul. 9, 2026.

* cited by examiner

UNIBODY RETRIEVAL BASKETS AND METHODS

CROSS-REFERENCE TO RELATED APPLICATION

A claim for priority is hereby made to the Aug. 18, 2022 filing date of U.S. Provisional Patent Application No. 63/399,196, titled UNIBODY RETRIEVAL BASKETS AND METHODS ("the '196 Provisional Application"). The entire disclosure of the '196 Provisional Application is hereby incorporated herein.

TECHNICAL FIELD

This disclosure relates generally to devices (e.g., medical devices, etc.) and device assemblies (e.g., medical device assemblies, etc.), for removing objects (e.g., stents, embolic devices, foreign bodies, pathology, emboli, thrombi, etc.) from small spaces (e.g., a location within a subject's body (e.g., their vasculature and/or other organs, including cavities, chambers, and/or other spaces therein, etc.), etc.). More specifically, this disclosure relates to so-called "revascularization devices" and "retrieval devices" with expandable baskets that may be used with catheters to remove objects from a subject's body. Even more specifically, the expandable basket of a medical device of this disclosure may include struts that rotate to facilitate engagement of an object to be removed from a subject's body. Methods for removing objects from a subject's body are also disclosed, as are methods for manufacturing medical devices.

RELATED ART

A variety of devices have been designed to remove objects from a subject's body. These devices are sometimes referred to as "revascularization devices" and "retrieval devices" or "retrievers." Many revascularization devices include retrieval structures that are introduced into or adjacent to an object that is to be removed from the body of the subject and then expanded to engage the object. With the object engaged by the retrieval structure, the revascularization device may be pulled from the subject's body, hopefully bringing the engaged object with it. Medtronic (SOLITAIRE X), Stryker (TREVO), and Cerenovus (EMBOTRAP II) manufacture revascularization devices with expandable structures.

The retrieval structures of existing revascularization devices typically comprise expandable mesh elements (e.g., tubes, etc.). Such an expandable mesh element may exert a radially outward force on an object to engage it. In addition, parts of the object may be received by openings of the expanded mesh element, which may further engage the object as it is removed from the body of the subject. The expandable mesh element and an object it engages may also be pulled proximally against the distal end of a catheter in an effort to trap the object between the expandable mesh element and the catheter, which may further facilitate removal of the object from the subject's body.

While existing retrieval devices are useful for removing some objects from a subject's body, their effectiveness is limited by their ability to engage an object. In an effort to improve the abilities of such devices to remove objects from subjects' bodies, expandable mesh elements with increasingly complex geometries have been designed. Nevertheless, the effectiveness of existing revascularization devices continues to be limited by the manner in which the retrieval structures of such devices interact with the objects that are to be retrieved.

SUMMARY

A retrieval device according to this disclosure comprises, consists essentially of, or consists of a tube with an expandable section at or adjacent to its distal end. The expandable section may comprise a basket. The basket may self-expand or a user may manually control its expansion.

The basket of the retrieval device may self-expand in any of a variety of suitable ways. For example, the basket may comprise a spring that collapses when it is radially constrained (e.g., when the basket is contained within the lumen of a catheter, etc.) and expands upon being released or freed from its radial constraint (e.g., by pushing the basket distally beyond the distal end of a catheter, etc.). Without limitation, such a basket (and, optionally, its associated tube) may be formed from stainless steel (e.g., 316L stainless steel, 316 stainless steel, etc.) or another suitable material (e.g., cobalt chromium (CoCr), a nickel chromium (NiCr or nichrome) alloy (including, without limitation, NiCr steel), etc.). As another example, the basket (and, optionally, its associated tube) may comprise a material with shape memory, which is in a collapsed state under a first condition (e.g., room temperature, etc.) or a first set of conditions (e.g., room temperature, under radial constraint, etc.) and assumes an expanded state upon being subject to a second condition (e.g., body temperature, etc.) or a second set of conditions (e.g., body temperature, being released from a radial constraint, etc.). Without limitation, such a basket (and, optionally, its associated tube) may be formed from a shape memory alloy (e.g., nitinol, etc.).

In embodiments where a user may manually expand the basket and, optionally, manually collapse the basket, the retrieval device may include an expansion control wire that extends through the tube and the basket, with a distal end of the expansion control wire being affixed to the tube of the retrieval device at a location on a distal side of the basket (e.g., to a distal end of the tube, etc.). Expansion of the basket may be achieved by pulling the expansion control wire proximally. The basket may collapse upon pushing the expansion control wire distally relative to the tube of the retrieval device and/or due to a resiliency of the basket (e.g., from one or more of the material from which the basket is formed, a configuration of the basket, etc.).

The basket may be defined by an arrangement of struts that rotate as the basket expands. More specifically, the struts may rotate from circumferential orientations to radial orientations as the basket expands. An outwardly (e.g., radially) oriented edge of the strut may have a configuration that enables it to cut into an object that is to be retrieved from a body of a subject. The struts may rotate from their radial orientations back toward or to their circumferential orientations as the basket collapses.

In some embodiments, the retrieval device may comprise a hypotube. The basket of the retrieval device may comprise an expandable section of the hypotube. The expandable section may include a plurality of slits that define struts. The slits may be arranged in a manner that allows the expandable section of the hypotube to expand from its native outer diameter (OD), or its unexpanded OD, to an expanded OD. The expanded OD of the occlusive device may be about twice or even about three times its native OD. The expandable section of the hypotube may also be shaped in a manner that ultimately enables it to expand to its predetermined final shape, or its desired occlusive shape. The expandable section may be bare or it may be coated with an expandable, resilient polymeric film.

A material of the hypotube may enable it and the basket defined by it to be constrained into a shape that facilitates its insertion into and/or removal from a body of a subject but expand upon removal of a constraining force. Without limitation, the hypotube may be made from a metal (e.g., a nitinol, a stainless steel, etc.) or a polymer (polyether ether ketone (PEEK), etc.).

In some embodiments, rows of slits may be defined along the length of the expandable section of the hypotube. Each row of slits may be positioned along a generator of the expandable section (i.e., a line extending from one end of an expandable section of the hypotube to the other end of the expandable section, parallel to an axis of the expandable section). Alternatively, each row of slits may be somewhat helically oriented around the hypotube. The slits of each row may be offset from the slits of an adjacent row. Each slit at an end of a length of the expandable section (and a length of the hypotube) may overlap about half of one slit of an adjacent row (e.g., a full slit at an end of the expandable section, etc.). Each slit at an intermediate location along a length of the expandable section (and a length of the hypotube) may overlap about half of each of two slit of an adjacent row. Stated another way, the slits of an expandable section may have a so-called "brickwork" arrangement, or they may be arranged like the bricks in a so-called "running bond pattern."

The remaining solid portions of the expandable section are its struts; thus, the slits define the struts of the expandable section. Each strut may extend along the length of the expandable section and, thus, along the length of the hypotube. The struts may be aligned with a longitudinal axis of the expandable section and/or a longitudinal axis of the hypotube. Alternatively, the struts may be helically oriented around the hypotube. Each strut may have an arcuate cross-sectional shape, taken transversely or perpendicularly to a longitudinal axis of the basket and/or a longitudinal axis of the tube.

The slits of the expandable section of the hypotube may be arranged in a manner that enables the struts to torque and/or twist or rotate as the expandable section or a portion thereof expands. Such an arrangement may also enable an expanded portion of the expandable section to return to an unexpanded state once an appropriate constraining force is applied to the hypotube (e.g., when an external force constrains the hypotube into a tube, the tube's diameter will decrease and the rotating struts will rotate back to a flat non-rotated position, etc.). With such an arrangement, when the expandable section is in a constrained state, or an unexpanded state, it may have a smooth outer surface, which may facilitate its movement through a catheter. As the expandable section expands and its struts rotate, the struts may engage an adjacent object, which may provide an additional mechanism for securing the object prior to its removal from the body of the subject (i.e., retrieval of the object). More specifically, as the struts rotate outwardly, their increasingly radial orientations and their exposed edges may enable them to extend into (e.g., cut into, etc.) or otherwise mechanically engage the object. In some embodiments, further engagement of the object may be achieved by at least partially collapsing the expandable section to cause the struts to rotate toward their circumferential orientations.

The slits of the expandable section of a hypotube may also be arranged in a manner that enables the struts of the expandable section to assume a desired final shape (e.g., a cylinder, a sphere, a symmetrical helix, an asymmetrical helix, or any other desired shape).

In another aspect, a retrieval device of this disclosure may be part of a medical device assembly or, more specifically, a retrieval assembly. The retrieval assembly may also include a catheter. The catheter may facilitate delivery of the retrieval device to a particular location within the body of a subject, such as a location from which an object is to be removed from the subject's body.

In addition to the retrieval device and the catheter, the retrieval device assembly may include a slider. The optional slider may be associated with a proximal end of the catheter to facilitate movement of the retrieval device along a length of the catheter. Thus, the slider may also enable expansion of the basket of the retrieval device by pushing the retrieval device distally and retraction of the basket by pulling the retrieval device proximally. Retraction of the basket may include pulling a proximal end of the expanded basket proximally toward or against the distal tip of the catheter, at least partially retracting the basket into a lumen of the catheter, or completely retracting the basket into the lumen of the catheter. Any of these actions may facilitate removal of the retrieval device and any object engaged or carried by the basket of the retrieval device from a body of a subject.

In addition to the retrieval device and the catheter, the retrieval device assembly may include a suction controller. The suction controller may comprise an enlarged element (e.g., a bulbous plug, etc.) that may be associated with a distal tip of the catheter to control the communication of suction beyond the distal tip of the catheter. In some embodiments, the suction controller may include an enlarged element that remains on a distal side of the basket. Such an enlarged element may be secured in place relative to a distal end of the tube of the retrieval device and, thus, on a distal side of the basket of the retrieval device. A size of the enlarged element may enable it to seat against and seal against the distal tip of the catheter to prevent suction applied to the catheter from being communicated and applied to the body of the subject until the enlarged element of the suction controller is advanced distally beyond the distal tip of the tube. The enlarged element of the suction controller may be secured to a distal end of the tube of the retrieval device; thus, distal advancement of the retrieval device relative to the catheter may distally advance the enlarged element away from the distal tip of the catheter. Alternatively, the suction controller may include a wire that extends through the tube of the retrieval device, with the enlarged element of the suction controller being secured to a distal end of the wire; thus, distal advancement of the enlarged element away from the distal tip of the catheter may be accomplished by advancing the wire distally relative to the retrieval device and/or by advancing the retrieval device distally relative to the catheter. Thus, such an embodiment of suction controller enables suction to be communicated beyond the distal tip of the catheter whenever the basket of the retrieval device is advanced (partially or completely) distally beyond the distal tip of the catheter.

In other embodiments, the suction controller may comprise an enlarged element that may enable control of suction beyond a distal end of the catheter regardless of whether the basket is located within the lumen of the catheter or advanced distally beyond the distal tip of the catheter. Such a suction controller may include an enlarged element on a proximal side of the basket. The enlarged element includes a lumen that receives a portion of the tube of the retrieval device, while limiting or preventing the communication of suction between an interior surface of the lumen and an exterior surface of a portion of the tube of the retrieval device located within the lumen. Such an arrangement may enable a user to selectively apply suction to a location from which an object is to be retrieved and/or to the object once the basket has been deployed from the distal end of the catheter.

In another aspect, this disclosure includes methods for retrieving objects from the body of a subject, including, without limitation, revascularization methods. Such a method includes advancing a basket of a retrieval device toward a location within a body of a subject from which an object is to be removed. The basket of the retrieval device may be positioned adjacent to the object (e.g., into or through the object, next to the object, etc.). The basket may expand as or after it is positioned adjacent to the object. As the basket expands to engage the object, struts of the basket rotate outwardly from circumferential orientations to radial orientations to facilitate further engagement of the object. In some embodiments, the expanded basket may be at least partially collapsed to enable the struts to even further engage the object; for example, by rotating at least partially toward their circumferential orientations to grasp the object. Once the basket engages the object, the basket and the retrieval device of which the basket is a part may be removed from the body of the subject, pulling the object with the retrieval device. Engagement of the object and its removal from the body may be facilitated by suction applied through a catheter used with the retrieval device.

A method for defining a medical device (e.g. a retrieval device or revascularization device, etc.) (e.g., from a shape memory alloy (e.g., nitinol, etc.), etc.) may include providing a tube (e.g., formed from the shape memory alloy, etc.), defining an expandable section (e.g., a basket, etc.) of the medical device from the tube, defining a processing access section from the tube, and imparting the expandable section with an expanded shape.

The expandable section and processing access section may be defined by cutting (e.g., laser cutting, etc.) a distal portion of the tube. The processing access section may comprise elongated cuts, or slits, that are substantially aligned around a circumference of the tube and continuous with and extend from an end (e.g., a proximal end, etc.) of the expandable section without extending to the end of the tube. Thus, the processing access section may comprise a temporarily expandable extension of the expandable section. The processing access section may open at a location adjacent to the end of the basket to eliminate the need for cutting the expandable section to facilitate further processing and, thus, to enable the formation of an expandable section with two constrained ends, or reduced diameter ends. More specifically, the processing access section may be opened to enable a forming mandrel to be introduced into the tube and positioned within the portion of the tube that will define the expandable section.

With the forming mandrel in place, a collar may be positioned over the processing access section to close the processing access section and reduce an outer diameter of the processing access section (e.g., so the outer diameter of the processing access section is substantially the same as an outer diameter of uncut portions of the tube, etc.). The tube, forming mandrel, and collar may then be processed (e.g., annealed, or heat set, etc.) in a manner known in the art to define an expanded shape of the expandable section and to ensure that the processing access section of the tube remains closed during use of the medical device.

Once processing is complete, the forming mandrel may be forced out of the expandable section, into the processing access section, and removed through a slit of the processing access section. Upon removal of the forming mandrel, the processing access section will spring back to its closed state, as defined by the collar during processing. Such a method may also be used to manufacture other types of medical devices with expandable sections. The formation and closure of a processing access section at an intermediate location of the tube (at a location where it does not extend to the end of the tube), the need to re-constrain an end of the expandable section with a collar, sleeve, weld, or bump and, thus, the potential for such a constraint to fail are eliminated.

Other aspects of the disclosed subject matter, as well as features and advantages of various aspects of the disclosed subject matter, should become apparent to those of ordinary skill in the art through consideration of the ensuing description, the accompanying drawings, and the appended claims.

DETAILED DESCRIPTION

Figure 1:
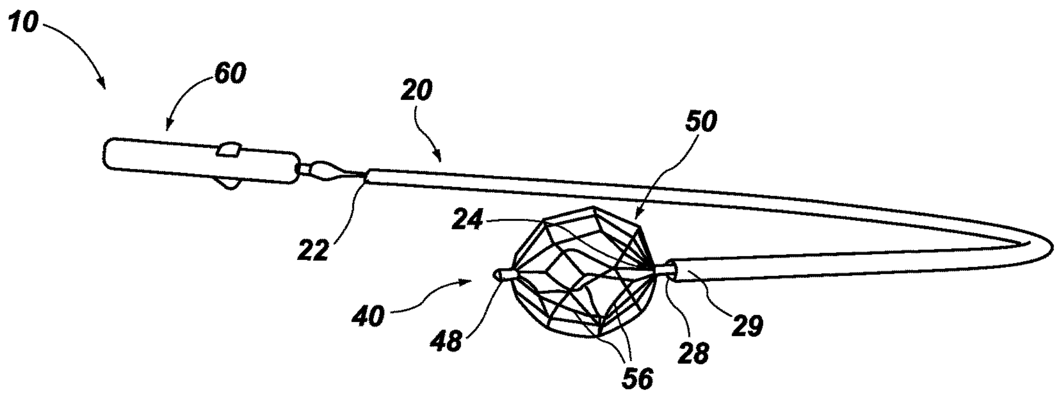
FIG. 1 is a perspective view of a medical device assembly that includes a catheter, an embodiment of a retrieval device, and an optional slider, showing an expandable section of the retrieval device, which may self-expand, deployed from a distal tip of the catheter.

With reference to FIG. 1, an embodiment of a medical device assembly 10 is depicted. The medical device assembly 10 includes a catheter 20 and an embodiment of a retrieval device 40. The medical device assembly 10 may also include a slider 70.

The catheter 20 may comprise any catheter suitable for use in the anatomy from which an object is to be retrieved (e.g., neurological vasculature, cardiac vasculature, etc.). More specifically, the catheter 20 may carry the retrieval device 40 to a desired location within the body of a subject or it may provide a pathway for advancement of the retrieval device 40 to the desired location within the body of the subject. The catheter 20 may also enable operation of the retrieval device 40, as well as facilitate the engagement of an object and removal of the object from the body of the subject.

The catheter 20 includes a proximal end 22 and a distal end 28. A distal tip 29 may be provided at the distal end 28 of the catheter 20. A lumen 24 extends through the catheter 20 along a length of the catheter 20, opening to and establishing communication between the proximal end 22 and the distal end 28.

The dimensions of the catheter 20 may be sufficient to aspirate a variety of objects from the body of a subject, including, without limitation, emboli, thrombi, tissue, pathology, embolic devices, stents, and the like. The catheter 20 may have an OD of about 0.020 inch (about 0.5 mm) to about 0.5 inch (about 12.7 mm) and a lumen 24 with an inner diameter (ID) of about 0.015 inch (about 0.4 mm) to about 0.450 inch (about 11.4 mm).

The retrieval device 40 is an elongated medical device. The retrieval device 40 may comprise a tube 41 with a proximal end 42, a distal end 48, a distal portion 46 adjacent to the distal end 48, and an intermediate portion 44 between the proximal end 42 and the distal portion 46. An expandable section 50, which comprises a basket of retrieval device 40, is defined at the distal portion 46 of the tube 41. Since the retrieval device 40, including its expandable section 50, may be defined from a single tube, the retrieval device 40 may be referred to as having a unitary construction or a “unibody” construction.

The tube 41 may be formed from any of a variety of suitable materials or from a combination of suitable materials. In some embodiments, the tube 41 may comprise a hypotube, which may be formed from a substantially rigid material, such as a metal. Examples of suitable metals include, but are not limited to, memory alloys (e.g., nitinol, etc.), cobalt chromium (CoCr), nickel chromium (NiCr or nichrome) alloys (including, without limitation, NiCr steel), stainless steel (e.g., 316L stainless steel, 316 stainless steel, etc.), and the like. Alternatively, the body 12 may be formed from a polymer. A suitable polymer may have a sufficient hardness (e.g., at least 35 Shore D, 35 Shore D to 55 Shore D, 35 Shore D to 72 Shore D, etc.). Examples of suitable polymers include, but are not limited to polyether ether ketone (PEEK), polyimide, nylon, polyether block amides (PEBA, such as that branded as PEBAX®), and extruded plastics (provided that they have a wall thickness that does not exceed the width of their struts 56, as explained below).

The tube 41 may have an ID that will accommodate a guidewire (e.g., a guidewire with an OD of about 0.010 inch (about 0.25 mm) to about 0.038 inch (about 0.97 m)). The tube 41 may have an OD of about 0.015 inch (about 0.4 mm) to about 0.450 inch (about 11.4 mm) and an ID of about 0.010 inch (about 0.25 mm) to about 0.440 inch (about 11.2 mm); i.e., an OD and an ID in any of the above-identified ranges.

Figure 2:
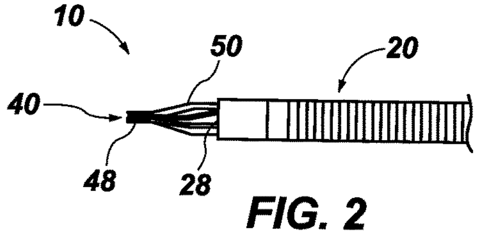
FIG. 2 is side view of a distal end of the embodiment of the medical device assembly shown in FIG. 1, with the expandable section of the retrieval device only partially distally advanced beyond the distal tip of the catheter.
Figure 5:
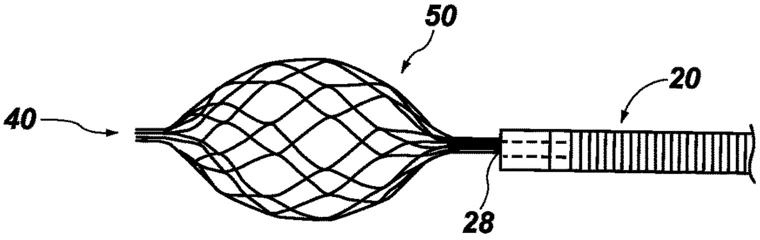
FIG. 5 is a side view of the distal end of the embodiment of the medical device assembly shown in FIG. 1, with the expandable section of the retrieval device distally advanced beyond the distal tip of the catheter and fully expanded.
Figure 6:
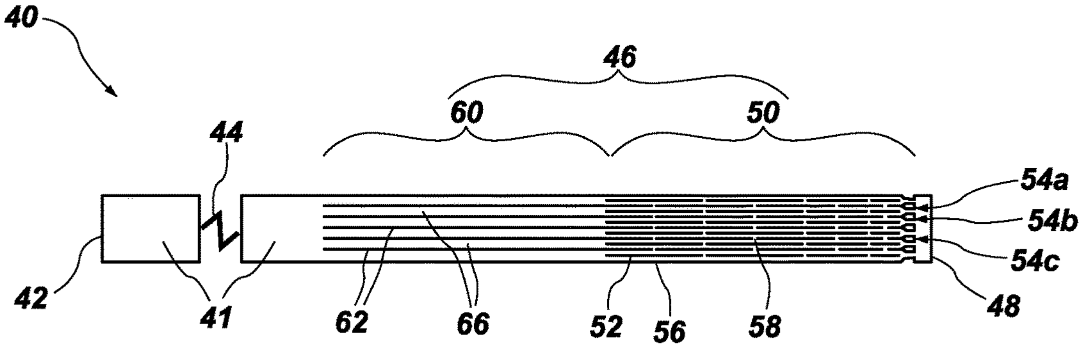
FIG. 6 is an engineering drawing showing features and dimensions of a specific embodiment of a retrieval device.

The expandable section 50 of the retrieval device 40 may be capable of expanding outward (e.g., radially outward, etc.) from an unexpanded state, as shown in FIGS. 2 and 6, to the expanded state and to a final shape shown in FIGS. 1 and 5. For example, in embodiments where the tube 41 is formed from a stainless steel or a polymer, the expandable section 50 may expand to its final shape upon removal of a constraining force from the expandable section 50. As another example, in embodiments where the tube 41 is formed from a shape memory material, such as a shape memory alloy, the expandable section 50 may expand to its final shape when exposed to appropriate conditions (e.g., body temperature, etc.). In yet another example, the expandable section 50 may be manually expanded.

Figure 3:
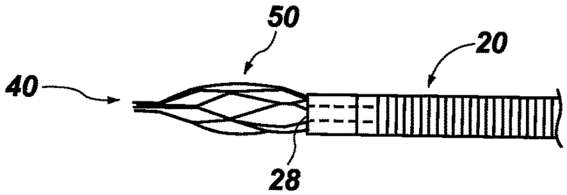
FIG. 3 is a side view of the distal end of the embodiment of the medical device assembly shown in FIG. 2, with the expandable section of the retrieval device further, but still only partially, distally advanced beyond the distal tip of the catheter and partially expanded.
Figure 4:
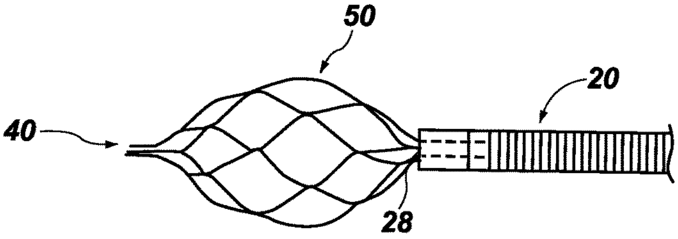
FIG. 4 is a side view of the distal end of the embodiment of the medical device assembly shown in FIG. 1, with the expandable section of the retrieval device completely distally advanced beyond the distal tip of the catheter.

FIGS. 2-5 progressively show distal advancement of the expandable section 50 of the retrieval device 40 through and beyond the distal end 28 of the catheter 20 and expansion of the expandable section 50 upon being removed from the constraints of the catheter 20. In FIG. 2, the distal end 48 of the tube 41 of the retrieval device 40 and a distal portion of the expandable section 50 emerge from the distal end 28 of the catheter 20. As distal advancement continues, more of the expandable section 50 emerges, as shown in FIG. 3. In embodiments where the expandable section 50 self-expands, it may expand as it exits the distal end 28 of the catheter 20, as is also shown in FIG. 3. As FIG. 4 shows, the expandable section 50 may fully expand once it has been distally advanced beyond the distal end 28 of the catheter 20. As illustrated by FIG. 5, the expandable section 50 may be further distally advanced beyond the distal end 28 of the catheter 20.

With returned reference to FIG. 1, a slider 70 may be associated with the proximal end 22 of the catheter 20 and the proximal end 42 of the tube 41 of the retrieval device 40. The slider 70 facilitates movement of the retrieval device 40 relative to the catheter 20 and may also facilitate movement of the catheter 20 relative to the retrieval device 40. The slider 70 may enable the retrieval device 40 to be distally advanced and/or proximally retracted, or pulled, relative to the catheter 20. More specifically, the slider 70 may enable distal advancement of the tube 41 of the retrieval device 40, which may enable the distal end 48 of the tube 41 and the expandable section 50 of the retrieval device 40 to distally advance through and beyond the distal end 28 of the catheter 20. Such distal advancement may occur as a user operates the slider 70. The slider 70 may also retract, or pull, the tube 41 proximally through the lumen 24 of the catheter 20 to at least partially retract the expandable section 50; for example, to further engage an object to be removed from a body of a subject. Such proximal retraction may occur as the user operates the slider 70 or it may be automatic (e.g., the slider 70 may include a spring arranged to pull the tube 41 proximally, etc.).

The slider 70 may be secured in place relative to the proximal end 22 of the catheter 20 while engaging the proximal end 42 of the tube 41 in a manner that facilitates movement of the retrieval device 40 along the length of the catheter 20. In some embodiments, the slider 70 may also be able to move the catheter 20 over the retrieval device 40 (e.g., by pulling the catheter 20 proximally, etc.).

Turning now to FIG. 6, a specific embodiment of an expandable section 50 of the retrieval device 40 is depicted. The expandable section 50 may be defined by series 54*a*, 54*b*, 54*c*, etc., of slits 52 that extend at least partially through a wall of the tube 41. In some embodiments, each slit 52 may extend completely through the wall of the tube 41, from its outer surface to its inner surface. In other embodiments, each slit 52 may extend only partially through the wall of the tube 41 (e.g., from the outer surface of the wall toward the inner surface of the wall, etc.). The extent to which each slit 52 extends through the wall of the tube 41 may depend, at least in part, upon the material from which the tube 41 is formed.

The slits 52 (with the exception of some slits 52 located at the ends of the expandable section 50) may have the same lengths as one another. Adjacent slits 52 in a series 54*a*, 54*b*, 54*c*, etc., are spaced apart by solid, uncut regions of the tube 41. These solid regions may be referred to as joints 58 or junctions.

Each series 54*a*, 54*b*, 54*c*, etc., may be defined by linearly aligned slits 52. The slits 52 and each series 54*a*, 54*b*, 54*c*, etc., may extend longitudinally along the tube 41, with each series 54*a*, 54*b*, 54*c*, etc., being positioned along a generator of the expandable section 50 (i.e., a line extending from one end of the expandable section 50 to the other end of the expandable section 50, parallel to a longitudinal axis of the expandable section 50). Such an orientation may be referred to as a "straight" orientation. Alternatively, each series 54*a*, 54*b*, 54*c*, etc., may be helically oriented around the tube 41.

The slits 52 of each series 54*b*, 54*c*, 54*d*, etc., may be offset relative to the slits 52 of each adjacent series 54*a*, 54*b*, 54*c*, 54*d*, 54*e*, etc. Each slit 52 in a series 54*a*, 54*b*, 54*c*, etc., may overlap about half of one (if the slit 52 is located at or near an end of the expandable section 50) or two (if the slit 52 is intermediately located along the length of the expandable section 50) circumferentially adjacent slits 52 of each adjacent series 54*a*, 54*b*, 54*c*, etc. Staggering of the slits 52 around the circumference of the expandable section 50 may provide the expandable section 50 with a so-called "brickwork" appearance, with solid portions of the tube 41 between the slits 52 arranged in a so-called "running bond pattern."

Circumferentially adjacent series 54*a*, 54*b*, 54*c*, etc., of slits 52 may be spaced equidistantly around the circumference of the tube 41. The expandable section 50 may include an even number of series 54*a*, 54*b*, 54*c*, etc., of slits 52. In embodiments where an even number of circumferentially adjacent series 54*a*, 54*b*, 54*c*, etc., of slits 52 are spaced equidistantly around the circumference of the tube 41, each slit 52 of the expandable section 50 may be staggered relative to its circumferentially adjacent slits 52. Alternatively, the distance between slits 52 of one circumferentially adjacent series 54*a* may differ from the distance between slits 52 of another circumferentially adjacent series 54*c*; thus, the number of slits 52 of one circumferentially adjacent series 54*a* may differ from the number of slits 52 of another circumferentially adjacent series 54*c*.

The solid portions of the tube 41 that are located between each adjacent pair of series 54*a* and 54*b*, 54*b* and 54*c*, 54*c* and 54*d*, etc., of slits 52 comprise struts 56 of the expandable section 50. More specifically, each strut 56 may comprise a solid portion of the tube 41 between adjacent series 54*a* and 54*b*, 54*b* and 54*c*, 54*c* and 54*d*, etc., of slits 52. Stated another way, each slit 52 comprises a gap between a pair of circumferentially adjacent struts 56. In embodiments where the series 54*a*, 54*b*, 54*c*, etc., are oriented along the longitudinal axis of the tube 41, the struts 56 may also be oriented along the longitudinal axis of the tube 41; in embodiments where the series 54*a*, 54*b*, 54*c*, etc., are helically oriented around the tube 41, the struts 56 may also be oriented helically, or as a spiral, around the tube 41.

Staggering of the slits 52 may enable the expandable section 50 to expand. As the expandable section 50 expands, the struts 56 may rotate. When the expandable section 50 is expanded, the struts 56 may rotate up to rotate 90°. Such rotation may occur in embodiments where each ring of circumferentially aligned struts 56 around an expandable section 50 includes an even number of struts 56. As the struts 56 rotate, their edges protrude outwardly (i.e., somewhat radially, substantially radially, radially, etc.) from the expandable section 50.

In a specific embodiment, such an expandable section 50 may expand to an OD of about 15 mm, with the slits 52 opening up to space adjacent struts 56 as much as about 2 mm to 8 mm apart from each other.

With continued reference to FIG. 6, the retrieval device 40 may also include a processing access section 60. The processing access section 60 is adjacent to and continuous with an end of the expandable section 50. As depicted, the processing access section 60 may be located on a proximal side of the expandable section 50.

The processing access section 60 may be defined from the tube 41 in the same manner as the expandable section 50. In addition, definition of the processing access section 60 may occur in conjunction with (e.g., concurrently with, immediately before, immediately after, etc.) definition of the expandable section 50.

The processing access section 60 may comprise elongated access slits 62, which may be continuous with at least some of the slits 52 at an end of the expandable section 50. The access slits 62 may be substantially aligned around a circumference of the tube 41 to define access struts 66 from the tube 41. The number and length(s) of the access slits 62 and access struts 66 may enable the processing access section 60 to be opened in a manner that facilitates processing of the tube 41 during manufacture of the retrieval device 40 therefrom. More specifically, an adjacent pair of access struts 66 on opposite sides of an access slit 62 may be pulled apart from each other to define an opening in the processing access section 60 of the tube 41.

In a specific embodiment, as depicted by FIGS. 7-10, the processing access section 60 may facilitate the introduction of a forming mandrel 80 into the expandable section 50 to define an expanded shape of the expandable section 50 (e.g., a shape the expandable section 50 assumes when no constraining force prevents its radial expansion, a shape an expandable section 50 formed from a shape memory material assumes upon being exposed to appropriate conditions, etc.). More specifically, the lengths of the slits 62 of the processing access section 60 may enable the slits 62 to be opened to a sufficient size to enable the forming mandrel 80 to pass therethrough. In such an embodiment, the processing access section 60 may also facilitate removal of the forming mandrel 80 from the expandable section 50 once the expanded shape of the expandable section 50 has been defined.

The forming mandrel 80 has a shape that defines an expanded shape of the expandable section 50. In addition, the forming mandrel 80 includes positioners 81 insertable into the tube 41 to determine its position and, thus, the position of the expanded shape of the expandable section 50, relative a longitudinal axis of the tube 41. While the forming mandrel 80 is depicted as being spherical with positioners 81 that position a center of the mandrel 80 along the longitudinal axis of the tube 41, the forming mandrel 80 may have other shapes. For example, the mandrel may be oval, cylindrical, or any other suitable shape. In addition, the positioners 81 may be positioned within the expandable section 50 at other locations (e.g., offset or off-center locations, etc.) relative to the longitudinal axis of the tube 41.

Figure 7:
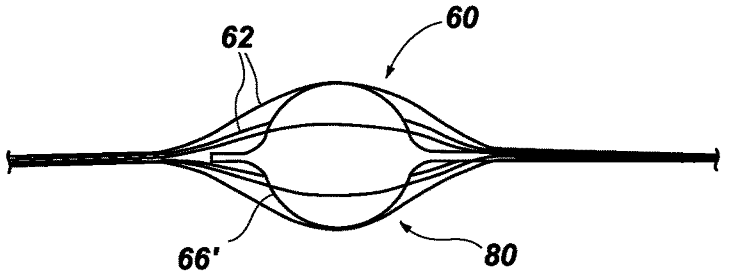
FIGS. 7-10 depict an embodiment of part of a method of manufacturing an expandable section of a medical device.

FIG. 7 shows the processing access section 60 in an open configuration, with a pair of access slits 66 having been moved apart from each other to expand the slit 62 (FIG. 6) therebetween into an opening 62' that accommodates a forming mandrel 80. As shown, introduction of the forming mandrel 80 into the processing access section 60 has expanded the processing access section 60.

Figure 8:
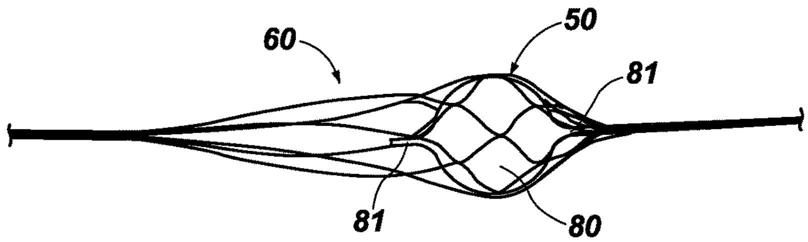

As shown in FIG. 8, the forming mandrel 80 is then forced distally into the expandable section 50, which forces the expandable section 50 to expand.

Figure 9:
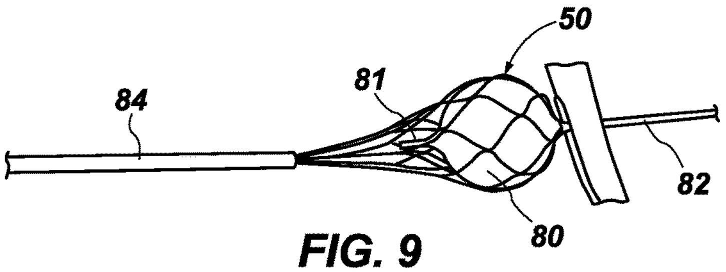

FIG. 9 shows the placement of a distal constraint 82 (e.g., a collar, etc.) on a distal side of the expandable section 50 to distally secure the forming mandrel 80 in place along the lengths of the expandable section 50 and tube 41.

Figure 10:
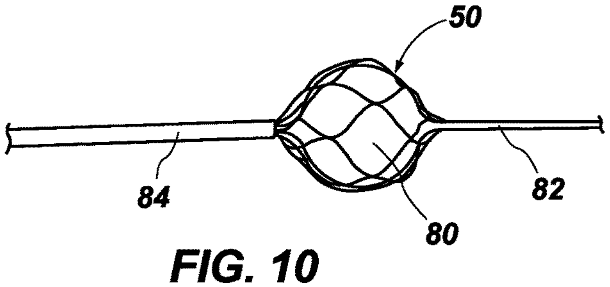

FIG. 10 shows the advancement of a proximal constraint 84 (e.g., a collar, etc.) into place over the processing access section 60 of the tube 41. The proximal constraint 84 further secures the forming mandrel 80 in place along the lengths of the expandable section 50 and tube 41.

Figure 11:
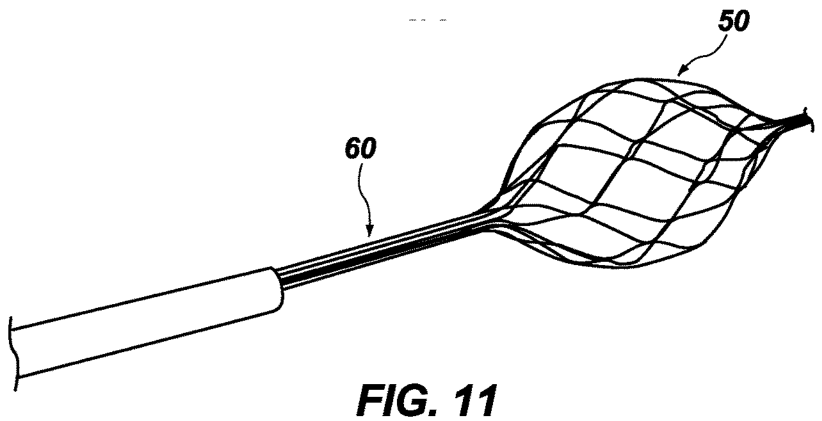
FIG. 11 depicts an embodiment of a medical device manufactured using the method depicted by FIGS. 7-10.

With the forming mandrel 80 in place within the expandable section 50, the tube 41 may be annealed in a manner known in the art to define the expanded shape of the expandable section, or the shape the expandable section 50 will assume when exposed to appropriate conditions (e.g., body temperature, etc.). Once the annealing process is complete, the distal constraint 82 and proximal constraint 84 may be removed and the forming mandrel 80 may be forced out of the expandable section 50, into the processing access section 60 (see FIG. 8), and removed through an opening 62' defined by a slit 62 of the processing access section 60. Upon removal of the forming mandrel 80, the processing access section 60 will spring back to its closed state, as seen in FIG. 11.

Figure 12:
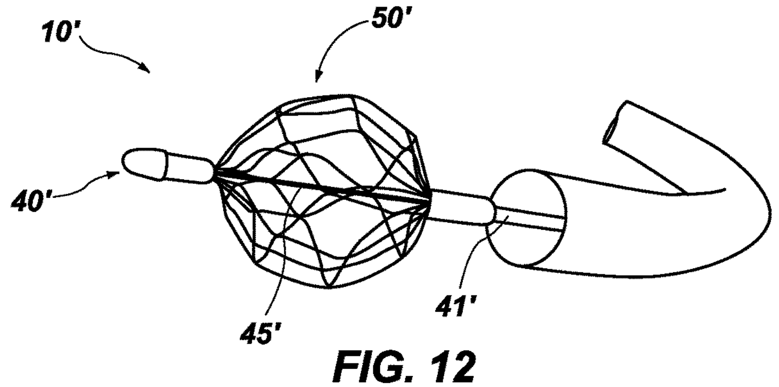
FIG. 12 is a partial perspective view of another embodiment of a medical assembly that includes a catheter and an embodiment of a retrieval device with an expandable section that is manually expandable and, optionally, collapsible.
Figure 13:
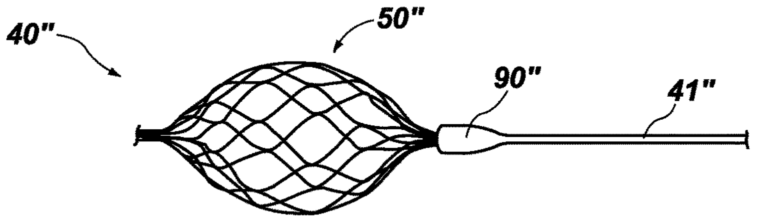
FIG. 13 shows a distal portion of an embodiment of a retrieval device that includes a suction controller on a proximal side of its expandable section.
Figure 14:
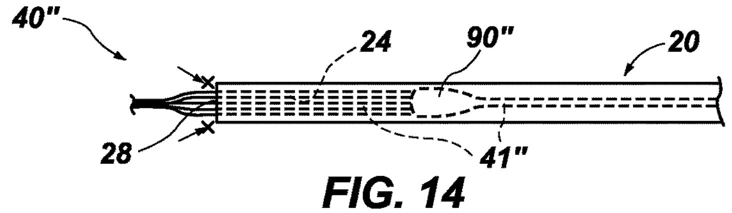
FIGS. 14-17 depict the manner in which the suction controller of the embodiment of the retrieval device shown in FIG. 13 functions as part of a medical device assembly, with FIGS. 14-16 showing how the suction controller limits or prevents the communication of suction applied to the lumen of the catheter beyond the distal end of the catheter as the expandable section of the retrieval device is distally advanced beyond the distal end of the catheter and FIG. 17 showing how the suction controller may be distally advanced beyond the distal end of the catheter and/or proximally pulled toward the distal end of the catheter to enable a user to control the amount of suction applied distally beyond the distal end of the catheter (e.g., to an object being retrieved, etc.)
Figure 15:
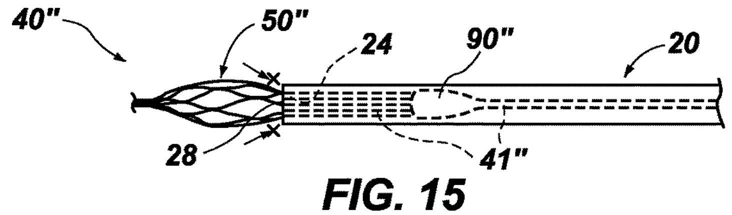
Figure 16:
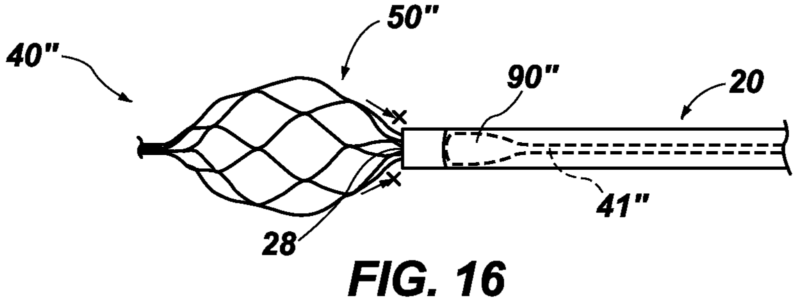
Figure 17:
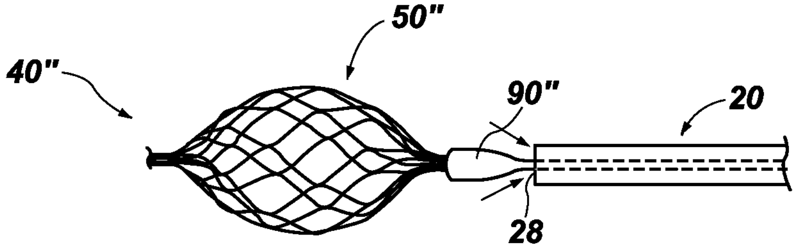
Figure 18:
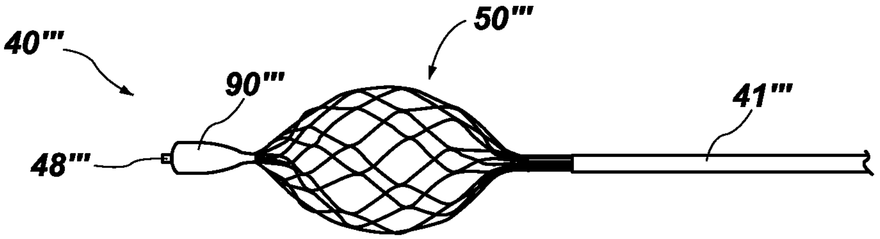
FIG. 18 shows a distal portion of an embodiment of a retrieval device that includes a suction controller on a distal side of its expandable section.
Figure 19:
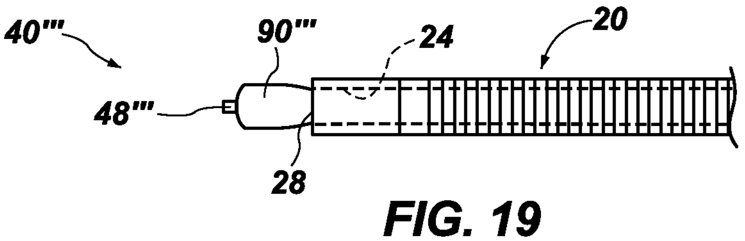
FIGS. 19-22 depict the manner in which the suction controller of the embodiment of the retrieval device shown in FIG. 18 functions as part of a medical device assembly and, more specifically, that suction applied to the lumen of the catheter is communicated beyond the distal end of the catheter as soon as the retrieval device and, thus, the suction controller is advanced distally relative to the catheter.
Figure 20:
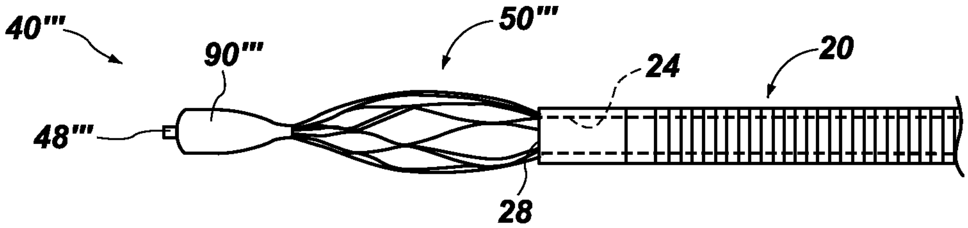
Figure 21:
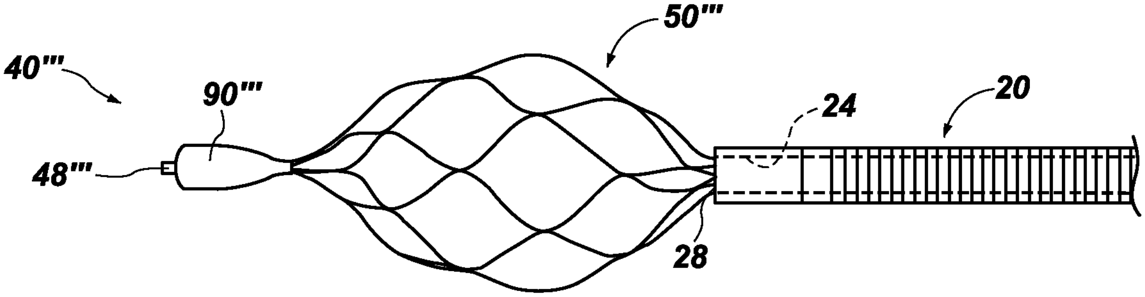
Figure 22:
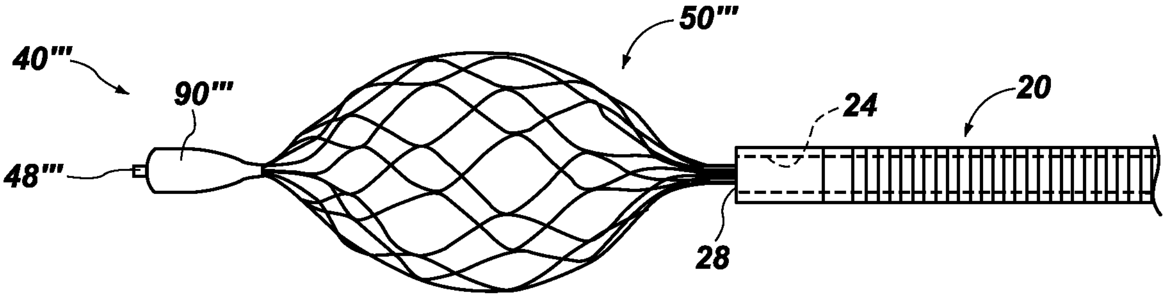

Turning now to FIG. 12, a medical device assembly 10' with a retrieval device 40' that includes a manually expandable embodiment of an expandable section 50' is depicted. The expandable section 50' is collapsed when no force is applied to it, but may radially expand when its length is shortened. The retrieval device 40' may include an expansion control wire 45' that extends through a tube 41' of the retrieval device 40' and the expandable section 50', with a distal end (not shown) of the expansion control wire 45' being affixed to the tube 41' at a location on a distal side of the expandable section 50' (e.g., to a distal end of the tube 41', etc.). Expansion of the expandable section 50' may be achieved by pulling the expansion control wire 45' proximally. The expandable section 40' may collapse upon pushing the expansion control wire 45' distally relative to the tube 41' and/or due to a resiliency of the expandable section 50' (e.g., from one or more of the material from which the expandable section 50' is formed, a configuration of the expandable section 50', etc.).

With returned reference to FIG. 1, in use, the distal end of the catheter 20 may be advanced to a desired location within the body of a subject, such as a location where an object is to be removed from the body of the subject. Such placement may include placement of the distal end 28 of the catheter 20 through the object or adjacent to the object until the expandable section 50 (in an unexpanded state within the lumen 24 of the catheter 20) is located within or adjacent to the object to be removed. The distal end 28 of the catheter 20 may then be retracted to expose the expandable section 50 to enable it to expand onto or into the object to be removed. Alternatively, such placement may include placement of the distal end 28 of the catheter at a location proximal to the object to be removed. The retrieval device 40 and its expandable section 50 may then be advanced from the distal end 28 of the catheter 20 to a location within or adjacent to the object to be retrieved. As the expandable section 50 expands, it engages the object to be retrieved.

As the expandable section 50 expands into or onto the object to be retrieved, its struts 56 may rotate outwardly, orienting edges of the struts 56 radially. Such an orientation reduces profiles of the struts 56, which may enable them to slice into and/or cut through some objects (e.g., fresh thrombi, semi-fresh thrombi, older thrombi, etc.).

Once the expandable section 50 engages the object to be removed, the expandable section 50 may be pulled against and/or partially into the distal end 28 of the catheter 20, which may trap the object between the retrieval device 40 and the catheter 20. In addition, retraction of the expandable section 50 may cause it to at least partially collapse, which may rotate its struts 56 back toward or to their circumferential orientations. Such rotation may grab and hold onto some objects (e.g., thrombi, emboli, pathology, stones, foreign bodies, etc.).

While the expandable section 50 engages the object, the object may be withdrawn from the body of the subject. Such removal may occur by aspirating the object through the tube 41 of the retrieval device 40 and/or the lumen 24 of the catheter 20, by pulling the retrieval device 40 proximally through the lumen 24 of the catheter 20, or by removing the entire medical device assembly 10 from the body of the subject.

With reference to FIGS. 13-22, in some embodiments, aspiration, or the application of suction, beyond the distal end 28 of the catheter 20 may be controlled upon movement of the retrieval device 40 relative to the catheter 20.

As depicted by FIGS. 13-17, a retrieval device 40" may include a suction controller 90". The suction controller 90" may comprise an enlarged element that may enable control of suction beyond a distal end of the catheter 20 regardless of whether the expandable section 50" is located within the lumen 24 of the catheter 20 or advanced distally beyond the distal end 28 of the catheter 20. Such a suction controller 90" may be located on a proximal side of the expandable section 50". The expandable section 90" includes a lumen (not shown) that receives a portion of the tube 41" of the retrieval device 40", while limiting or preventing the communication of suction between an interior surface of the lumen 24 and an exterior surface of a portion of the tube 41" of the retrieval device 40" located within the lumen 24. Such an arrangement may limit the communication of suction beyond the distal end 28 of the catheter 20 until the expandable section 50" is fully deployed, as shown in by the small arrows and x's in FIGS. 14 and 15, and then enable a user to selectively apply suction to a location from which an object is to be retrieved and/or to the object once the expandable section 50" has been deployed from the distal end 28 of the catheter 20, as shown by the small arrows and x's in FIG. 16 (limited suction) and the large arrows in FIG. 17 (full suction), by distally advancing the retrieval device 40''' or proximally withdrawing the catheter 20.

FIGS. 19-22 show an embodiment of a retrieval device 40''' with a suction controller 90''' on a distal side of the expandable section 50'''. Such a suction controller 90''' may comprise an enlarged element secured in place relative to a distal end 48''' of the tube 41''' of the retrieval device 40''' and, thus, on a distal side of the expandable section 50''' of the retrieval device 40'''. A size of the suction controller 90''' may enable it to seat against and seal against the distal end 28 of the catheter 20 to prevent suction applied through the lumen 24 of the catheter 20 from being communicated and applied to the body of the subject until the suction controller 90''' is advanced distally beyond the distal end 28 of the catheter 20. The suction controller 90''' may be secured to a distal end 48''' of the tube 41''' of the retrieval device 40"; thus, distal advancement of the retrieval device 40''' relative to the catheter 20 may distally advance the suction controller 90''' away from the distal end 28 of the catheter 20. Such an embodiment of suction controller 90''' enables suction to be communicated beyond the distal end 28 of the catheter 20 whenever the expandable section 50''' of the retrieval device 40''' is advanced distally or the catheter 20 is withdrawn proximally, regardless of whether the expandable section 50''' has been partially or fully deployed beyond the distal end 28 of the catheter 20.

As depicted, the suction controller 90", 90''' may have a somewhat parabolic shape. Alternatively, the suction controller 90", 90''' may be spherical or ovoid in shape. The suction controller 90", 90''' may be formed from a material (e.g., a relative hard rubber, etc.) that will seal against the lumen 24 and/or the distal end 28 of the catheter 20. Arrangements such as those depicted by FIGS. 13-22 enable a user to instantly turn aspiration on and substantially turn aspiration off and/or slow aspiration by simply moving the retrieval device 40", 40''' or the catheter 20.

Figure 23:
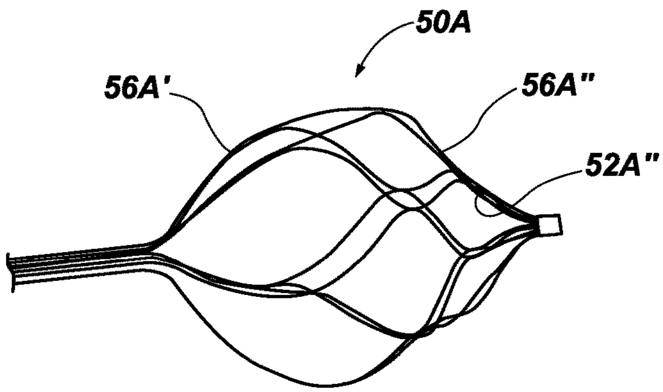
FIGS. 23-25 illustrate various embodiments of expandable sections, or baskets, of retrieval devices according to this disclosure.
Figure 24:
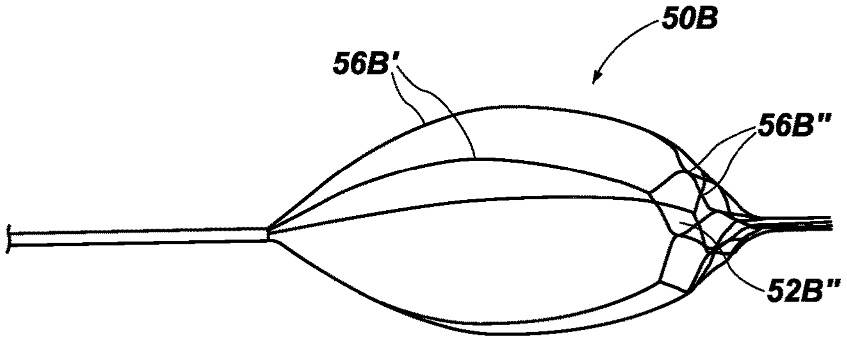
Figure 25:
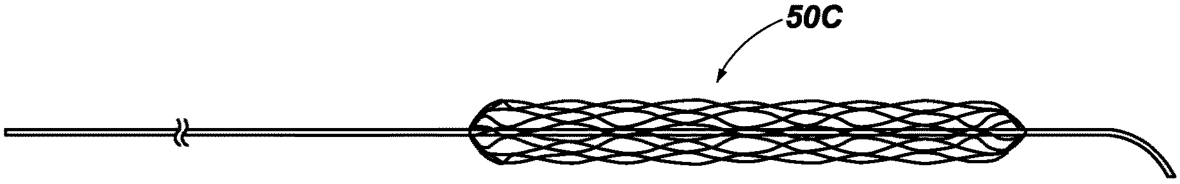

Turning now to FIGS. 23-25, alternative embodiments of expanded expandable sections 50A, 50B, and 50C are respectively shown. The embodiment of expandable section 50A shown in FIG. 23 includes long, relatively straight struts 56A' on a proximal side thereof, and shorter struts 56A" and, thus, smaller openings 52A" on the distal side thereof. Such a configuration may enable the proximal side of the expandable section 50A to expand into a soft object, such as a blood clot, and the proximal side of the expandable section 50A to withdraw the object into a catheter 20 (not shown). The embodiment of expandable section 50B shown in FIG. 24 includes similar features to those of the embodiment of expandable section 50A shown in FIG. 23, with the proximally located struts 56B' being even longer and the distally located struts 56B" being shorter and their associated openings 52B" being even smaller.

The embodiment of expandable section 50C shown in FIG. 25 is elongated. Such an embodiment may be useful for engaging and removing elongated objects (e.g., stents, blood clots, etc.) from the body of a subject.

A retrieval device of this disclosure may be used in a variety of contexts. In addition to medical and veterinary uses, the retrieval devices may be used in construction, manufacturing, research, lab, aerospace, petroleum, and consumer markets where there is a need to improve aspiration force and control over the removal of fluids, liquids, gases, plasmas, and solids.

Although this disclosure provides many specifics, these should not be construed as limiting the scope of any of the claims that follow, but merely as providing illustrations of some embodiments of elements and features of the disclosed subject matter. Other embodiments of the disclosed subject matter, and of their elements and features, may be devised which do not depart from the spirit or scope of any of the claims. Features from different embodiments may be employed in combination. Accordingly, the scope of each claim is limited only by its plain language and the legal equivalents thereto.

What is claimed:

1. A retrieval device for engaging and removing an object from a small space, comprising:
- a tube; and
- an expandable section defined in a distal section of the tube, the expandable section including an arrangement of slits of equal length defining a plurality of struts that rotate from circumferential orientations to radial orientations and move apart from each other at a plurality of locations around a circumference of the expandable section to form openings of equal size that are axially offset from each other upon expansion of the expandable section to engage the object and that move toward each other and rotate back toward the circumferential orientations upon at least partially collapsing the expandable section to grasp the object.

2. The retrieval device of claim 1, wherein the expandable section is self-expandable.

3. The retrieval device of claim 1, wherein the expandable section is manually expandable.

4. The retrieval device of claim 1, wherein the tube comprises a hypotube.

5. The retrieval device of claim 4, wherein the hypotube comprises a metal hypotube.

6. The retrieval device of claim 5, wherein the metal hypotube comprises a shape memory alloy.

7. The retrieval device of any of claim 1, further comprising:
- a processing access section adjacent to and continuous with the expandable section, the processing access section comprising access slits continuous with at least some slits of the expandable section, the processing access section having an outer diameter that is substantially the same as an outer diameter of the tube.

8. The retrieval device of claim 1, wherein the arrangement of struts comprises a brickwork arrangement.

9. The retrieval device of claim 1, further comprising:
- a suction controller on the tube.

10. The retrieval device of claim 9, wherein the suction controller is located on a distal side of the expandable section.

11. The retrieval device of claim 9, wherein the suction controller is located on a proximal side of the expandable section.

12. A medical device assembly, comprising:
- a retrieval device comprising:
  - a tube; and
  - an expandable section defined in a distal section of the tube, the expandable section including an arrangement of slits defining a plurality of struts that rotate from circumferential orientations to radial orientations and move apart from each other to define openings of equal size at a plurality of locations around a circumference of the expandable section that are axially offset from each other and upon expansion of the expandable section to engage the object and that move toward each other and rotate back toward the circumferential orientations upon at least partially collapsing the expandable section to grasp the object; and a catheter with a lumen that receives the retrieval device, including the expandable section thereof.

13. The medical device assembly of claim 12, further comprising:

a slider that moves the retrieval device relative to the catheter.

14. The medical device assembly of claim 13, wherein the slider also moves the catheter relative to the retrieval device.

15. A method for retrieving an object from a small space, comprising:

advancing a distal end of a catheter into the small space, adjacent to a location of the object;

deploying an expandable section of a retrieval device from the distal end of the catheter, with the expandable section of the retrieval device expanding to define a plurality of openings of equal size at a plurality of locations around a circumference of the expandable section that are axially offset from each other to engage the object; and with the object engaged, removing the object from the body of the subject.

16. The method of claim 15, wherein advancing the distal end of the catheter into the small space comprises advancing the distal end of the catheter into or slightly beyond the object.

17. The method of claim 16, wherein deploying the expandable section of the retrieval device comprises withdrawing the catheter while the expandable section remains substantially in place.

18. The method of claim 15, wherein:

advancing the distal end of the catheter into the small space comprises advancing the distal end of the catheter to a location proximal to the object; and deploying the expandable section of the retrieval device comprises distally advancing the expandable section from the distal end of the catheter.

19. The method of claim 15, wherein removing the object comprises proximally retracting the expandable section toward or at least partially into the catheter.

20. The method of claim 15, further comprising:

selectively applying suction to the object by moving the retrieval device and/or the catheter.

21. A method for manufacturing an expandable device, comprising:

defining an expandable section of the expandable device from a tube, including forming a plurality of slits of equal length around a circumference of the tube at an array of locations that are axially offset from each other;

defining a processing access section from the tube adjacent to and continuous with the expandable section;

opening the processing access section;

introducing a forming mandrel into the processing access section;

forcing the forming mandrel from the processing access section into the expandable section, including opening the plurality of slits at the array of locations;

constraining the mandrel within the expandable section, including constraining the processing access section in a collapsed arrangement with a collar;

annealing the expandable section and the processing access section to define an expanded shape of the expandable section and to maintain the processing access section in the collapsed arrangement.

22. The method of claim 21, further comprising, after the annealing:

forcing the forming mandrel from the expandable section into the processing access section after opening the processing access section; and removing the forming mandrel from the processing access section.

* * * * *